US006809811B2

(12) United States Patent
Johnsen et al.

(10) Patent No.: US 6,809,811 B2
(45) Date of Patent: Oct. 26, 2004

(54) PROTECTIVE SHIELD FOR AN INSTRUMENT PROBE

(75) Inventors: Howard A. Johnsen, Livermore, CA (US); James R. Ross, Oakley, CA (US); Sal R. Birtola, San Jose, CA (US)

(73) Assignee: Sandia National Laboratories, Livermore, CA (US)

( * ) Notice: Subject to any disclaimer, the term of this patent is extended or adjusted under 35 U.S.C. 154(b) by 286 days.

(21) Appl. No.: 10/107,853

(22) Filed: Mar. 26, 2002

(65) Prior Publication Data

US 2003/0184746 A1 Oct. 2, 2003

(51) Int. Cl.[7] ............................................... G01J 3/00
(52) U.S. Cl. ..................... 356/300; 359/509; 356/318
(58) Field of Search ............................ 356/300, 318, 356/72–73; 359/509, 507

(56) References Cited

U.S. PATENT DOCUMENTS 5,599,105 A * 2/1997 Ridley et al. ............... 359/509
6,175,676 B1 * 1/2001 Sharan ....................... 356/72

* cited by examiner

Primary Examiner—F. L. Evans
Assistant Examiner—Kara Geisel
(74) Attorney, Agent, or Firm—Timothy P. Evans

(57) ABSTRACT

A shield is disclosed that is particularly useful for protecting exposed optical elements at the end of optical probes used in the analysis of hazardous emissions in and around an industrial environment from the contaminating effects of those emissions. The instant invention provides a hood or cowl in the shape of a right circular cylinder that can be fitted over the end of such optical probes. The hood provides a clear aperture through which the probe can perform unobstructed analysis. The probe optical elements are protected from the external environment by passing a dry gas through the interior of the hood and out through the hood aperture in sufficient quantity and velocity to prevent any significant mixing between the internal and external environments. Additionally, the hood is provided with a cooling jacket to lessen the potential for damaging the probe due to temperature excursions.

17 Claims, 3 Drawing Sheets

PROTECTIVE SHIELD FOR AN INSTRUMENT PROBE

STATEMENT OF GOVERNMENT INTEREST

This invention was made with U.S. Government support under contract no. DE-AC04-94AL85000 awarded by the U.S. Department of Energy to Sandia Corporation for the management and operation of Sandia National Laboratories. The Government has certain rights in the invention, including a paid-up license and the right, in limited circumstances, to require the owner of any patent issuing in this invention to license others on reasonable terms.

BACKGROUND OF THE INVENTION

The present invention relates to a device for transmitting and receiving light from a remote sample. More particularly, the present invention relates to a system for cooling a manifold containing a high energy optical probe used for measuring the optical response of a remote sample to a high energy stimulus.

The ability to monitor particulate matter in process streams and emissions to the air from industrial operations, and particularly the ability to do so in-situ and in real-time, is becoming increasingly important in many industrial processes. This is the case not only because of the desire to control and modify various processes in real-time to improve their efficiency but also to comply with various environmental regulations governing the composition and quantity of various industrial emissions.

In particular, atmospheric emissions of hazardous and/or regulated materials is now strictly controlled by certain state and federal regulatory authorities. Not only are industrial operations required to closely monitor their air emissions but they are also required to do so on a continuous basis. Measurement of concentrations of hazardous materials in stack emissions, however, is a difficult task. Currently, air emissions from industrial operations are measured using extractive sampling followed by off-line chemical analysis, a procedure that is costly and typically having analysis times ranging from days to weeks. Moreover, because certification tests require that more than one sample be taken for a given operating condition the many manual operations involved in extractive sampling introduce a significant potential for sampling error. The long turnaround times inherent in extractive sampling prevent the use of manual air emissions measurements as a realistic method for controlling operating parameters in real-time.

A wide variety of instruments are currently available for on-line analysis of flow streams. However, the optical probes that these instruments use are typically designed for analysis of the concentration of constituents in fluid streams. Furthermore, many of these instruments employ beam dividers or splitters, an arrangement which causes more than 75% of the available light to be lost. Because of the requirement for a second probe that receives light transmitted through the sample, instruments that operate in the transmittance mode are generally unsuited for use in the harsh environments of stack emissions from boilers, incinerators, furnaces and the like.

A method for circumventing many of the problems associated with analysis delays and sampling errors was disclosed in commonly owned U.S. Pat. No. 5,953,120 (herein incorporated by reference). Here, a compact optical probe is provided that is useful for analysis of stack emissions in industrial environments by means of laser spark spectroscopy. The geometry of the prior art optical probe provides a means for making optical measurements in environments where it is difficult and/or expensive to gain access to the vicinity of a flow stream to be measured. However, since this probe is exposed to the environment of the flow stream the optical elements at the probe end inserted into the flow stream suffers from ash fouling. Furthermore, this probe cannot be placed into flow streams where temperatures may exceed more than about a few hundred degrees Fahrenheit.

For the reasons set forth above, it is highly desirable to have an optical probe that permits measurements to be made at a plurality of locations within a flow stream, is rugged enough to be used for monitoring emissions from industrial boilers, incinerators and furnaces and can introduce an optical input of sufficient intensity into the flow stream to heat an entrained particle to a plasma and thus induce an optical response. It is further desired that the probe should be reliable, easy to handle and operate, and robust enough for continuous unmanned operation within a dirty, hostile environment.

The present invention provides an optical probe whereby all of its optical components (source, detector, relay optics, etc.) are either located external to the flow stream being monitored or protected by isolating them from the external stack environment thereby permitting a rugged and robust system. The geometry of the optical probe disclosed herein thus provides a means for making optical measurements in environments where it is difficult and/or expensive to gain access due to the hostile natures of the flow stream, making it particularly useful for remote sampling operations in industrial environments.

SUMMARY OF THE INVENTION

The prior art optical probe modified by the present invention comprises a laser spark spectroscopy system for directing a focused incident light beam onto a plurality of analysis locations within a flow stream, creating a spark discharge in the flow stream to ionize any entrained particle or particles, and collecting a return light beam from each of the plurality of analysis locations. The improvement to the optical probe includes a means for shrouding and purging the end of the probe inserted into the flow stream. The optical probe also includes an optical fiber means for receiving light from the return light beam in the vicinity of the final focusing lens.

In one aspect of the present invention, the optical probe includes a cowl or shield at the insertion end of the probe that further includes an orifice, or aperture, through which the incident beam may interact with an effluent flow stream and through which some of the emitted light created by the interaction may be collected. This embodiment is particularly advantageous, because it completely protects sensitive exposed optical surfaces from the contaminating effects of the flow stream ash particulate matter. This embodiment also provides conditions around the insertion end of the probe that do not significantly disturb the surrounding local flow stream environment.

In another aspect of the present invention the shield includes an interior wall that terminates in a conical funnel-section adjacent to the probe aperture.

In still another aspect of the present invention the shield is purged with a dry gas such a dry air or nitrogen.

In another aspect of the present invention the probe aperture is sized to provide only so much clearance as is necessary to permit focusing the laser optics at a point up to several feet beyond the laser source and to permit acquisition of the return light signal by an optical fiber situated at the periphery of the final focusing lens.

In another aspect of the present invention the shield includes a water cooled jacket.

In yet another aspect of the present invention the cooling jacket extends the full length of the probe.

DETAILED DESCRIPTION OF THE INVENTION

Figure 1A:
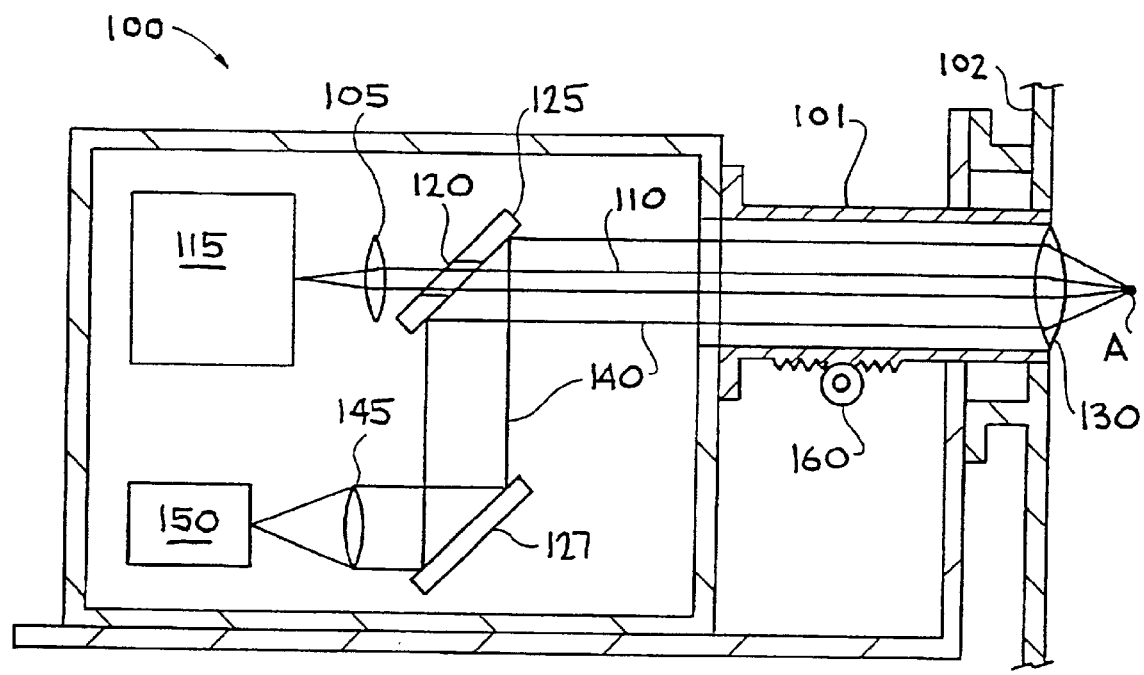
FIGS. 1A and 1B show schematic illustrations of embodiments of two possible prior art optical probes.

The present invention provides an improved optical probe useful for measuring the optical response of a particle that is heated and ionized by a high power energy source. For the purposes of the present discussion it is understood that the term "particle" is meant to include a single particle, or an ensemble of particles that may comprise any or all of solid matter such as dust, smoke, or fly ash; liquid droplets such as an aerosol; and "gaseous" complexes of organic and/or inorganic species such as VOC's (volatile organic compounds), organometallic compounds, and compounds of heavy metals.

The improvement of the present invention generally comprises an optical probe that includes a cowling or shield covering the end of the probe that is placed in the flow stream during operation; the shield being designed to protect the optical surfaces of the probe from the contaminating effects of the matter entrained in the flow stream.

The principal of operation of the optical probe is well known in the art. In particular, a short discussion is presented in commonly owned U.S. Pat. No. 5,777,734, issued Jul. 7, 1998 and U.S. Pat. No. 5,953,120 issued Sep. 14, 1999 and herein incorporated by reference. The prior art technique uses a pulsed laser to rapidly heat either a single particle, or an ensemble of particles, to produce a plasma (or laser "spark") that dissociates and ionizes some of the atoms comprising the particle. As the plasma cools, the excited species relax and decay through a specific sequence of energy states emitting optical energy at frequencies that are characteristic of the emitting elements at each energy state. Spectrally resolved measurements of these emissions can be used to identity and quantify the elements comprising the particle.

Regardless of the probe design, however, all need to project a high intensity high power, focused beam of light into the monitored flow stream in order to heat and ionize some portion of the atoms comprising one or more particles entrained in the stream and thereafter detect the light response emitted by the ionized atoms as each decay to successively lower energy states. To accomplish this, an optical window must be provided allowing the light beam to enter the flow stream while isolating the analysis equipment from the stream. Generally, one end of the probe itself is placed some distance into the flow stream and a final focusing lens provides the clear aperture as well as the isolation protection.

Unfortunately, most, if not all, monitored sites comprise an effluent stack delivering a sizable quantity of hot particulate ash that has a strong tendency to quench, and deposit onto any obstructing surface within its path. It has been observed that prior art optical probes are quickly fouled in use and require frequent removal and cleaning in order to maintain the aperture. However, even with frequent cleaning, operation between cleanings is none-the-less subject to the continuous degrading effects of surface deposits making it difficult to obtain reproducible measurements over time since the quantity of light passing back through the aperture to the probe photodetectors is heavily influenced by the degree to which the probe lens is coated with particulate ash.

To solve this problem, an ingenious shrouding structure or member has been designed to fit over the end of the prior art optical probe to prevent entrained ash from making contact with any of the optical surfaces of the probe.

Figure 1B:
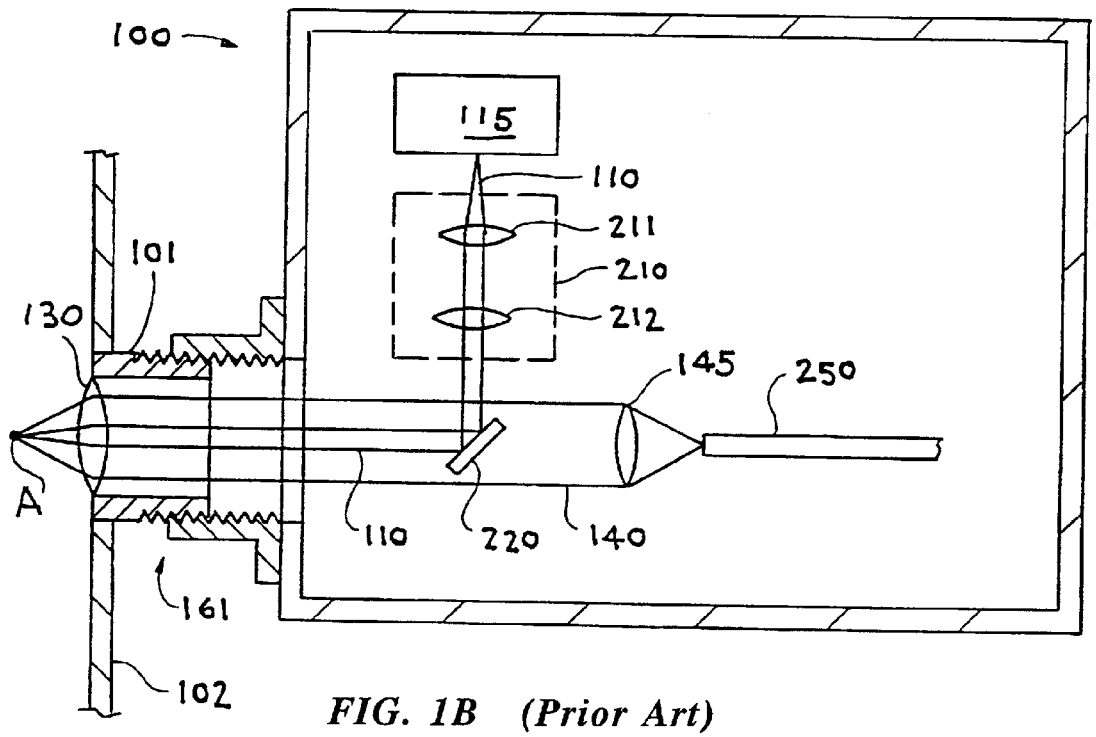

Two embodiments of the prior art optical probe are shown in FIGS. 1A and 1B. A descriptive account of the various components comprising these probes is provided in order to help clarify the operation of the probe and the manner in which the present invention operates in cooperation with these devices. In the illustrates optical probe 100 is shown penetrating an industrial stack 102 wherein focusing lens 130 can be translated by mechanical means 160 or 161 such that new analysis locations can be acquired. Here, light beam 110, issues from high energy light source 115, typically an Nd-YAG Q-switched laser, and is collimated by collimating lens 105 or by beam expanding telescope 210 consisting of lenses 211 and 212. The collimated beam 110 then passes through an aperture 120 in a mirror 125, or re-directed by mirror 220. Collimated beam 110 can then be focused by focusing lens 130 onto any selected point A within the stack, for analysis of the particles instantaneously entrained within a volume around selected point A at any particular time at which light source 115 is operated. A portion of the optical response of the particles within the volume around point A re-enter through lens 130 to be re-formed and collimated into returning light beam 140. Returning light beam 140 is reflected by mirrors 125 and 127 and directed onto lens 145. which act to provide a means for focusing returning light beam 140 onto light transmitting sensor 150, which can be the face of a optical fiber cable 250 that transmits light beam 140 to a detection means (not shown). New analysis points $A_i$ (where i=1, 2, ..., n) within the stack can be acquired by translating lens 130 such that the focal point of lens 130 is focused on a different analysis point $A_i$ (not shown). No other changes in the optical probe are required.

Figure 2:
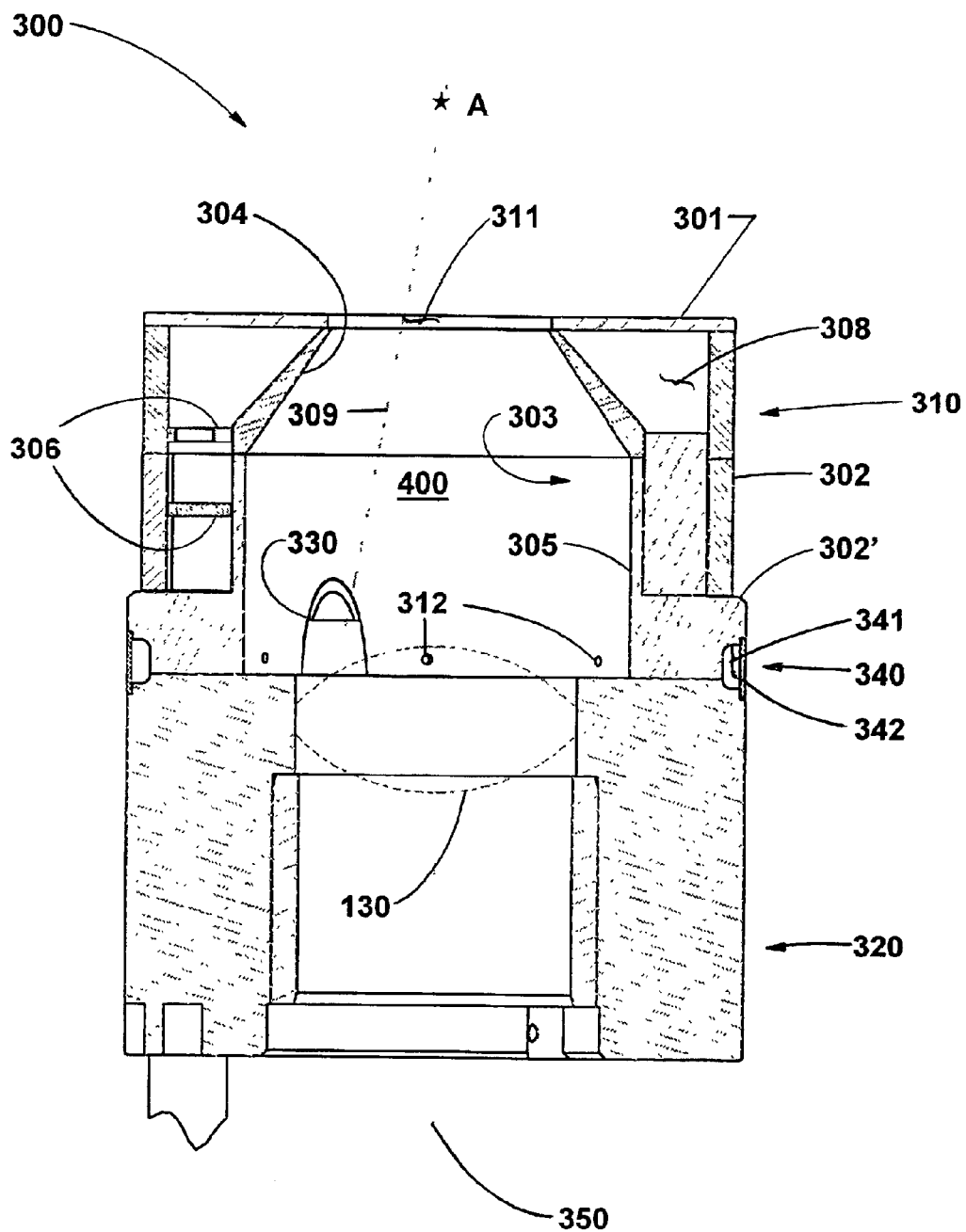
FIG. 2 shows a schematic illustration of an embodiment of the present invention showing the location of the gas plenum and gas distribution means as well as the angled conduit for holding the optical fiber.

To protect focusing lens 130 from ash deposition the end of probe tube 101 is re-configured, as shown in FIG. 2, to include shield 300. In its simplest form shield 300 comprises a metal shell opened at one end to cover the sensitive optical elements at the distal end of the probe inserted into the effluent stream. At the opposite end of this metal shell a smaller opening is provided as a clear aperture for the focused light beam exiting final focusing lens 130. The shield, therefore, provides several inches of separation between the optics of the probe and the external stack environment.

However, by itself simply covering and separating the probe optics from the stack environment is not sufficient to prevent fouling of the lens surfaces. A second strategy is provided that includes a blanketing layer of flowing gas that is used to significantly lessen the extent to which the atmosphere in stack environment mixes with the atmosphere contained within the interior region enclosed by the shield. To accomplish this a gas plenum is hermetically sealed to a region of the shield exterior and connected with a gas line with which to feed gas into the plenum. Several small ports or orifices are cut through the wall of the metal shell of the shield such that each opens to the gas plenum. Gas can then be moved through the gas line, into the plenum and orifices into the interior region enclosed by the shield and out through the opening provided in the end of the shield for the light beam.

Finally, to prevent damage due to high temperature excursions the shield is fitted with a cooling jacket within which to circulate a cooling fluid such as water.

EXAMPLE

Shield 300, therefore, is described as follows. Front and rear housing portions 310 and 320, are provided wherein front portion 310 itself comprises co-axial inner and outer shells 303 and 302 joined together at a rearward end by a common base portion 302' and at a forward end with cover 301 to provide a large enclosed interior region 400 surrounding the probe optical elements. In addition, inner and outer shells 303 and 302 are held apart from one another through a plurality of internal struts 306 to provide a first internal manifold 308 that, when connected with fluid input and output lines (not shown) through which a cooling media can be introduced, manifold 308 acts as a cooling jacket. Importantly, cover 301 includes clear opening 311 to allow a beam of light, focused by lens 130 along a central axis 350, to exit shield 300 and also to allow passing of a flowing stream of dry gas from the interior region 400 of shield 300.

The critical feature of the present invention is the ability to isolate interior region 400 from the stack environment while maintaining a clear aperture for transmitting and receiving a light signal. To accomplish this the invention provides a means for passing a quantity of dry gas from the interior of shield 300 and out through opening 311. To accomplish this, interior shell 303 is provided with forward and rear wall portions 304 and 305, wherein forward portion 304 comprises a funnel-shaped surface extending from the inside edge of opening 311 to rear wall 305. Furthermore, to provide a means for flowing gas through interior region 400, gas plenum 340 is provided along the perimeter of base portion 302' and hermetically joined to a gas input line. Plenum 340 is formed by cutting a recessed channel 341 into base portion 302' and covering and hermetically sealing recessed channel 341 by welding or brazing a covering band 342 along the two edges of channel 341. Plenum 340 is then placed in fluid communication with interior region 400 by a single row of evenly spaced ports or orifices 312 disposed around the perimeter of inner shell 303, penetrating rear wall 305 and connecting interior region 400 with plenum 340. Gas, typically dry nitrogen, dry air, or the like, can then be fed through plenum 340 into interior region 400 and out of opening 311. Funnel-shaped forward wall 304 acts to concentrate and provide a generally streamline plug flow of gas passing through opening 311. The cone angle of the funnel end of the wall is not particularly critical, but generally depends on the size of opening 311 and the mass flow rate of the gas exiting the opening. As noted, the intent is to provide generally laminar plug flow, i.e., flow having a low Reynolds number (generally below about $N_{Re}$=1500). Flow in this range generally minimizes turbulence at the opening and thus minimizes mixing between the stack environment and the shield interior effectively isolating the optical surfaces of the probe from the stack environment without unduly constraining the probe aperture.

Finally, shield 300 further comprises a further feature: an angled conduit 330 passing through outer shell 302 and interior shell 303 through which an optical fiber (not shown) may be passed in order to gain access to interior region 400. Conduit 330 is positioned near the periphery of focusing lens 130 so that central axis 309 of conduit 330 passes directly through focal point A of lens 130. The purpose of the optical fiber is to receive a portion of the light produced by the ionizing plasma created by the laser spark. This configuration eliminates many of the components described by the prior art optical probes and allows the user to configure a probe of nearly any useful length.

The principle of operation of the shield configured probe is as follows. The optical probe configured with the protective shield is readied for insertion into an effluent flow stream by initiating a flow water through manifold 308 (if the temperature of the environment requires cooling), and a flow of dry gas through a series of ports or orifices 312 penetrating interior shell 303 and issuing from an integral plenum (not shown) contained between inner and outer shells 303 and 302 and disposed along the perimeter of the outer shell. Dry gas is thus directed into interior region 400 in sufficient quantity to provide a protective barrier against the migration of effluent particles in the flow stream into the interior region of the probe shield where they might deposit on optical surfaces. The amount and rate of gas flow is dependent upon the size of opening 311 which is itself dependent on the aperture of focusing lens 130 and the position and angle of conduit 330 in order that the focused laser beam can exit shield 300 unimpeded and so that the detecting optical fiber has an unobstructed view of the focus region. In the present invention the distance from lens 130 to the outside surface of cover 301 is about 2 inches while the diameter of opening 311 is about 0.94 inches. Other dimensions are of course possible, but the overall intent is to provide a reasonable volume within which to build a plug flow of gas out through opening 311 while maintaining a clear field of view for both focusing lens 130 and the optical fiber deployed in conduit 330 when focused on point A. The flow of gas is maintained below a flow rate that would interfere with the natural flow of matter within the effluent flow stream but high enough to provide isolation from any convective mass transfer through gas mixing. A rate of about 12 liters/minute was found to be effective in the present invention but fractionally higher or lower values are likely to be as effective.

Figure 3A:
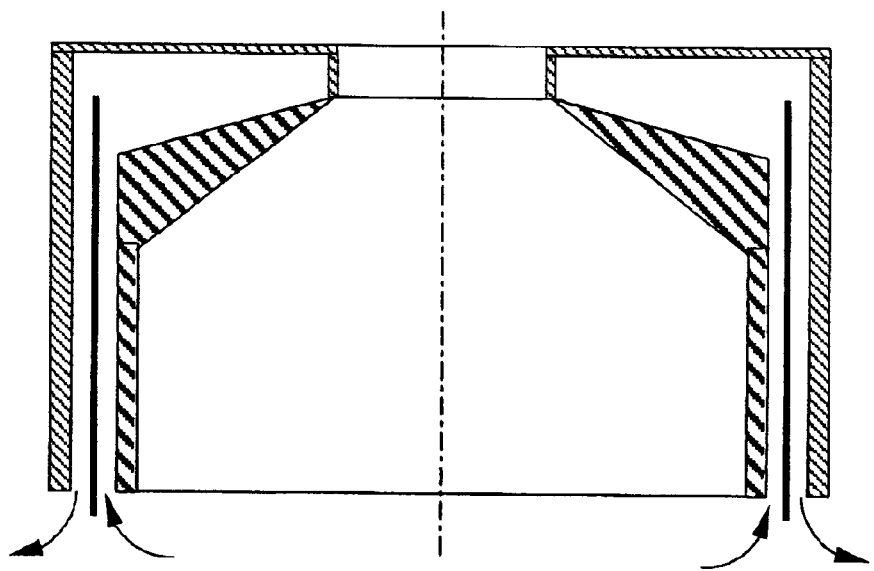
FIGS. 3A and 3B show cutaway illustrations of two possible configurations of the end of the probe shield of the present invention illustrating the cooling jacket.
Figure 3B:
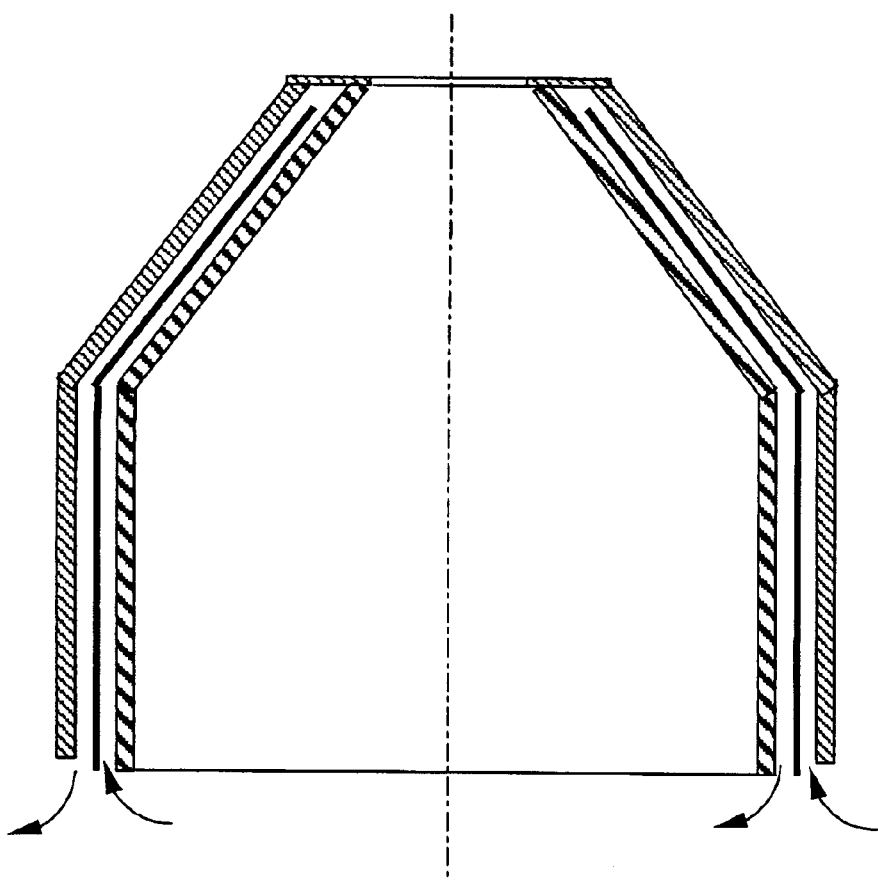

Once inserted into the effluent flow stream the primary laser is activated and low frequency pulse operation (~10 Hz) begun. As effluent particles are captured within the plasma generated at the laser beam focal point and ionized the characteristic light emissions given off by the atom as it returns to a ground state are collected by the optical fiber inserted into conduit 330 and returned to a standard light photometer/spectrometer for analysis. Additionally, the cooling medium circulating through manifold 308 and the gas flowing out of interior region 400, isolate and protect the optical elements within the end of the probe from the degrading effects of the hot gas and particles in the effluent stream. FIGS. 3A and 3B show cutaway illustrations of two possible configurations of the end of the probe shield of the present invention illustrating the cooling jacket. Other configurations are of course possible. The arrows shown in the illustrations show the path of the cooling medium as it enters and leaves the shield end.

From the foregoing description and examples, therefore, one skilled in the art can readily ascertain the essential characteristics of the present invention. In particular, it will be appreciated that the shield of the present invention can be also be used with any of a variety of other optical techniques that rely on measuring an optical response in a hostile environment. Optical techniques for which the improvement to an optical probe provides an advantage comprise: laser spark spectroscopy, Raman scattering, laser-induced fluorescence, Rayleigh scattering, Mie scattering and laser-induced incandescence. The description and examples are intended to be illustrative of the present invention and are not to be construed as limitations or restrictions thereon, the invention being delineated in the following claims.

We claim:

1. A shield for protecting an optical probe, comprising:
a shell partially enclosing an interior region, said shell comprising:
   a base portion engaging an end portion of said optical probe;
   a forward housing joined to said base portion;
   an opening through said forward housing providing a clear aperture for a focused beam of light directed through said optical probe, said beam of light defining an optical axis;
   a light collection means disposed at an angle to said optical axis and disposed about an axis oriented to intersect a point of focus of said beam of light;
a plenum disposed about and hermetically sealed to a perimeter of said shell;
a gas input means hermetically engaged to said plenum;
a plurality of spaced orifices disposed along said perimeter, said orifices passing through said shell into said plenum placing said plenum in fluid communication with said interior region; and
means for moving a quantity of gas from said gas input means into said interior region and out through said opening.

2. The shield of claim 1, wherein said shell further comprises forward and rear wall interior portions.

3. The shield of claim 2, wherein the forward wall interior portion comprises a funnel shaped surface extending from said opening to said rear wall portion.

4. The shield of claim 2, wherein said plurality of spaced orifices pass through said rear wall interior portion and into said gas plenum.

5. The shield of claim 4, wherein said plurality of spaced orifices are evenly spaced and disposed in a single row around a perimeter of said rear wall interior portion.

6. The shield of claim 1, further comprising a conduit passing through said shell at said angle, said conduit joined to said shell along a junction formed between said shell and said conduit surface.

7. The shield of claim 6, wherein said light collection means is disposed within said conduit.

8. The shield of claim 7, wherein said light collection means includes an optical fiber or a bundle of optical fibers.

9. The shield of claim 1, further including a cooling jacket, said cooling jacket comprising a manifold and means for circulating a cooling liquid into and out of said manifold.

10. A shield for protecting an end of an optical probe, comprising:

an inner shell comprising a wall and a base flange, said inner shell joined to an end portion of said optical probe;
an outer shell surrounding said inner shell, said outer shell resting on and joined to said base flange;
a cover extending from an outside edge of said outer shell to an inside edge of said inner shell, said cover joined to said inner and outer shells providing thereby an enclosed manifold therebetween, said inner shell and said cover delineating an interior region;
an opening delineated by the junction between said inner shell and said cover, said opening providing a clear aperture for a focused beam of light directed through said optical probe;
an axis extending through said interior region and about which said inner and outer shells are disposed, said axis coinciding with an optical axis of said optical probe;
a gas plenum hermetically joined to and disposed about said base flange;
a gas input means in fluid communication with said plenum; and means for communicating a gas from said plenum into said interior region;
a plurality of spaced orifices uniformly disposed along a perimeter of said inner shell distal to said opening and passing through said inner shell and into said gas plenum, said plurality of orifices for providing means to inject a quantity of dry gas into said interior region and out through said opening; and
a light collection means disposed at an angle to said optical axis and disposed about as axis oriented to intersect a point of focus of said beam of light.

11. The shield of claim 10, wherein said inner shell wall further comprises forward and rear wall interior portions.

12. The shield of claim 11, wherein the forward wall interior portion comprises a funnel shaped surface extending from said junction between said cover and said inner shell and said rear wall interior portion.

13. The shield of claim 11, wherein said plurality of spaced orifices are evenly spaced and disposed in a single row around a perimeter of said rear wall interior portion.

14. The shield of claim 10, further comprising a conduit passing through said inner and outer shells at said angle, said conduit joined to said inner and outer shells along first and second junctions formed between said inner and outer shells and an outside surface of said conduit.

15. The shield of claim 14, wherein said light collection means is disposed within said conduit.

16. The shield of claim 15, wherein said light collection means includes an optical fiber or a bundle of optical fibers.

17. The shield of claim 10, wherein said enclosed manifold includes means for circulating a cooling liquid into and out of said manifold.

* * * * *